United States Patent
Yahagi et al.

(10) Patent No.: US 11,730,343 B2
(45) Date of Patent: Aug. 22, 2023

(54) ENDOSCOPE TREATMENT TOOL AND ENDOSCOPE SYSTEM

(71) Applicants: OLYMPUS CORPORATION, Tokyo (JP); Naohisa Yahagi, Tokyo (JP)

(72) Inventors: Naohisa Yahagi, Tokyo (JP); Yasuhiro Tabuchi, Tokyo (JP); Yuya Hidaka, Tokyo (JP)

(73) Assignees: OLYMPUS CORPORATION, Tokyo (JP); Naohisa Yahagi, Tokyo (JP)

( * ) Notice: Subject to any disclaimer, the term of this patent is extended or adjusted under 35 U.S.C. 154(b) by 448 days.

(21) Appl. No.: 16/990,088

(22) Filed: Aug. 11, 2020

(65) Prior Publication Data
US 2020/0367727 A1    Nov. 26, 2020

Related U.S. Application Data

(63) Continuation of application No. PCT/JP2018/006677, filed on Feb. 23, 2018.

(51) Int. Cl.
*A61B 1/00* (2006.01)
*A61B 1/018* (2006.01)

(52) U.S. Cl.
CPC ........ *A61B 1/00087* (2013.01); *A61B 1/0014* (2013.01); *A61B 1/00089* (2013.01);
(Continued)

(58) Field of Classification Search
CPC ............ A61B 1/00089; A61B 1/00098; A61B 1/00101; A61B 1/018
See application file for complete search history.

(56) References Cited

U.S. PATENT DOCUMENTS

| | | | | |
|---|---|---|---|---|
| 8,226,544 B2 * | 7/2012 | Muyari | .............. | A61B 18/1492 |
| | | | | 600/129 |
| 8,602,970 B2 * | 12/2013 | Muyari | .................. | A61B 1/018 |
| | | | | 600/129 |

(Continued)

FOREIGN PATENT DOCUMENTS

| EP | 1 607 037 A1 | 12/2005 |
|---|---|---|
| EP | 3 009 086 A1 | 4/2016 |

(Continued)

OTHER PUBLICATIONS

International Search Report dated Apr. 24, 2018 received in PCT/JP2018/006677.

*Primary Examiner* — Matthew J Kasztejna
(74) *Attorney, Agent, or Firm* — Scully, Scott, Murphy & Presser, P.C.

(57) ABSTRACT

An endoscope treatment tool includes: a cylindrical cap attached to an outer side of a distal-end section of an endoscope and having first and second radial directions intersecting each other; a treatment tool supported at an outer side of the cap in the first radial direction to be movable in the longitudinal direction; and a linear flexible coupling member coupling the treatment tool with the cap such that the grasper reaches a position where the grasper protrudes from a distal end of the cap. A swing section of the coupling member couples the cap with the treatment tool to allow relative movement in the second radial direction, and, in response to pressed forward in the longitudinal direction by the treatment tool, swings about a swing axis extending in the second radial direction while generating a tensile force and bending the treatment tool inward in the first radial direction.

20 Claims, 7 Drawing Sheets

(52) U.S. Cl.
CPC ...... *A61B 1/00098* (2013.01); *A61B 1/00101* (2013.01); *A61B 1/00112* (2013.01); *A61B 1/018* (2013.01)

(56) References Cited

U.S. PATENT DOCUMENTS

| | | | |
|---|---|---|---|
| 9,649,015 B2* | 5/2017 | Okada | A61B 1/0014 |
| 2003/0040657 A1 | 2/2003 | Yamaya et al. | |
| 2005/0267335 A1 | 12/2005 | Okada et al. | |
| 2009/0259141 A1* | 10/2009 | Ewers | A61B 1/018 |
| | | | 600/106 |
| 2016/0029875 A1 | 2/2016 | Dkada | |
| 2016/0073859 A1 | 3/2016 | Kogiso et al. | |
| 2017/0105797 A1 | 4/2017 | Mikkaichi | |

FOREIGN PATENT DOCUMENTS

| | | |
|---|---|---|
| EP | 3 064 121 A1 | 9/2016 |
| EP | 3 167 833 A1 | 5/2017 |
| JP | 6-114075 A | 4/1994 |
| JP | 2003-210389 A | 7/2003 |
| JP | 2005-334237 A | 12/2005 |
| WO | 2014/199759 A1 | 12/2014 |
| WO | 2015/064616 A1 | 5/2015 |
| WO | 2016/006407 A1 | 1/2016 |

\* cited by examiner

ENDOSCOPE TREATMENT TOOL AND ENDOSCOPE SYSTEM

CROSS-REFERENCE TO RELATED APPLICATIONS

This is a continuation of International Application PCT/JP2018/006677, with an international filing date of Feb. 23, 2018, which is hereby incorporated by reference herein in its entirety.

TECHNICAL FIELD

The present invention relates to an endoscope treatment tool and an endoscope system.

BACKGROUND ART

There is a known connecting tool that attaches a guide tube for guiding a treatment tool to a distal end of an insertion portion of an endoscope (for example, see PTL 1).

According to this connecting tool, the distal end of the treatment tool guided through the guide tube, which is disposed radially outside the insertion portion of the endoscope, is disposed inside the field of view of the endoscope, and treatment can be performed on an affected area while observing the distal end of the treatment tool.

CITATION LIST

Patent Literature

{PTL 1} Japanese Unexamined Patent Application, Publication No. 2005-334237

SUMMARY OF INVENTION

A first aspect of the present invention provides an endoscope treatment tool including: a cylindrical cap that is attached to an outer side of a distal-end section of an endoscope, the cylindrical cap having a first radial direction and a second radial direction intersecting each other; a treatment tool that has, at a distal end, a grasper for grasping living tissue, the treatment tool being disposed, at an outer side of the cap in the first radial direction, along a longitudinal direction of the cap, the treatment tool being supported by the cap, at a position closer to a proximal end than the grasper is, so as to be movable in the longitudinal direction; and a coupling member that is configured to the treatment tool with the cap such that the grasper reaches a position at which the grasper protrudes from a distal end of the cap, the coupling member having a linear shape and flexibility, wherein the coupling member has a swing section that is disposed outside the cap and that is supported by the cap so as to be swingable about a swing axis extending in the second radial direction; and the swing section couples the cap with the treatment tool so as to allow relative movement in the second radial direction, and, in response to pressed forward in the longitudinal direction by the treatment tool moved forward in the longitudinal direction, swings about the swing axis while generating a tensile force and bending the treatment tool inward in the first radial direction.

A second aspect of the present invention provides an endoscope system including: an endoscope; and one of the above-described endoscope treatment tools.

DESCRIPTION OF EMBODIMENTS

An endoscope treatment tool 1 and an endoscope system 100 including the same according to one embodiment of the present invention will be described below with reference to the drawings.

Figure 1A:
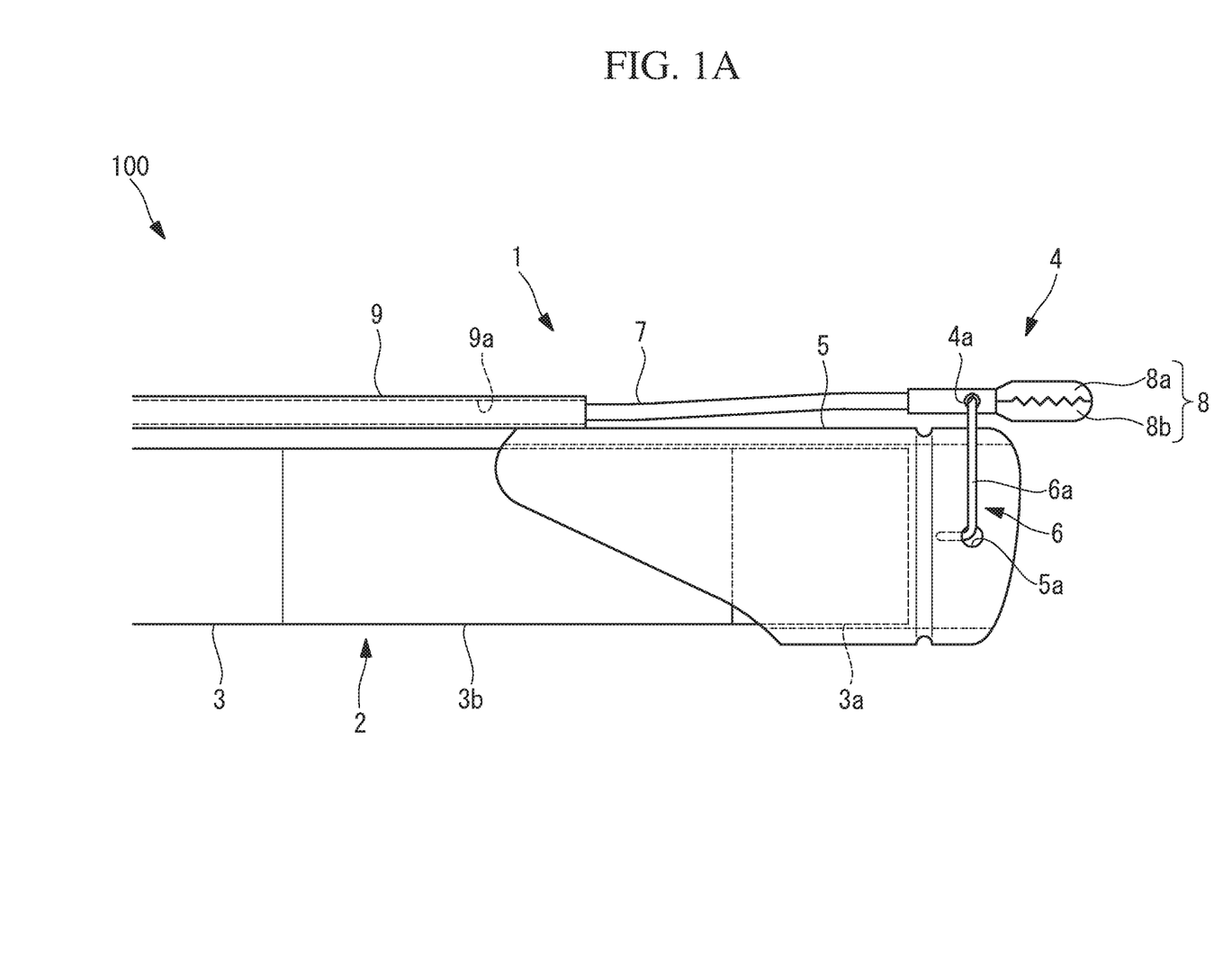
FIG. 1A is a side view showing the configuration of an endoscope treatment tool and an endoscope system according to one embodiment of the present invention.
Figure 1B:
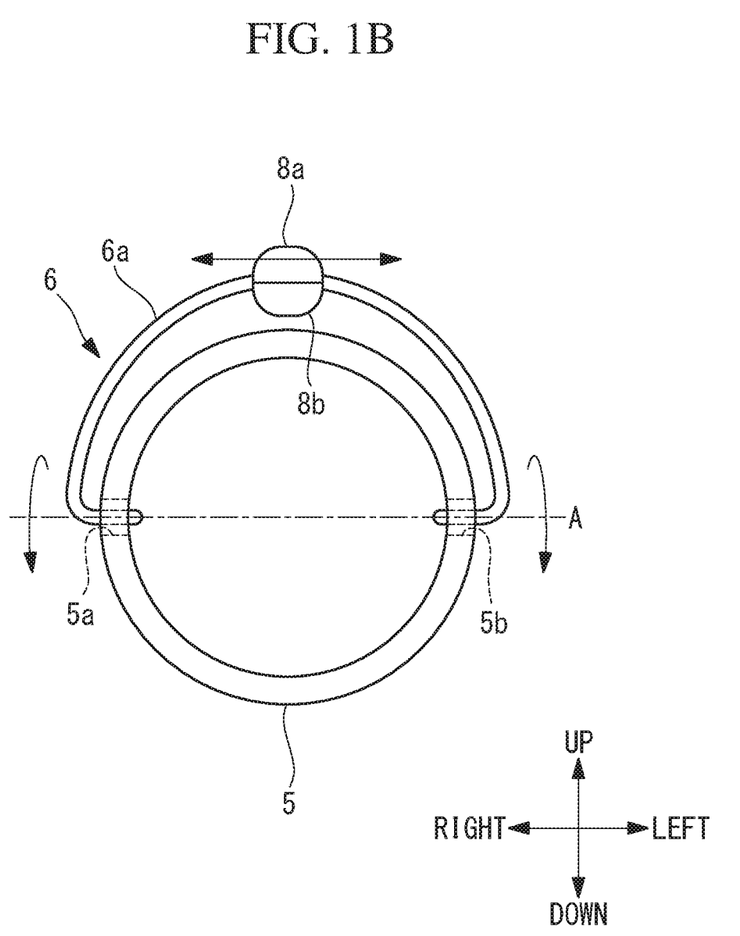
FIG. 1B is a front view of the endoscope treatment tool shown in FIG. 1A, viewed from a distal end thereof in the longitudinal direction.

As shown in FIGS. 1A and 1B, the endoscope system 100 of this embodiment includes: an endoscope 2 that has a long insertion portion 3 to be inserted into a body; and an endoscope treatment tool 1 that can be detachably attached to a distal-end section of the insertion portion 3.

The insertion portion 3 has: a hard distal-end rigid section 3a that includes a distal-end surface of the insertion portion 3 and that incorporates a lens etc.; and a bending section 3b that is adjacent to a proximal end of the distal-end rigid section 3a and that can be bent. The insertion portion 3 has an up-down direction and a left-right direction that are each perpendicular to the longitudinal axis and that are perpendicular to each other. The up-down direction and the left-right direction of the insertion portion 3 correspond to the up-down direction and the left-right direction of an endoscopic image. The bending section 3b can be bent at least in the left-right direction.

The endoscope treatment tool 1 includes: a treatment tool 4, such as grasping forceps; a substantially cylindrical cap 5 that can be detachably attached to an outer side of the distal-end section of the insertion portion 3 and that supports the treatment tool 4; and a linear coupling member 6 that couples the treatment tool 4 with the cap 5.

The treatment tool 4 includes a long body part 7 and a grasping part 8 that is connected to a distal end of the body part 7, and is disposed at a radially outer side of the cap 5 along the longitudinal direction of the cap 5.

The body part 7 has flexibility at least at a distal-end section thereof disposed closer to the distal end than a support part 9, to be described later, is.

The grasping part 8 has a pair of grasping pieces 8a and 8b that can open and close with respect to each other, thus making it possible to grasp living tissue between the pair of grasping pieces 8a and 8b.

The cap 5 is made of an elastic material, such as elastomer, and is open at a distal-end surface thereof and a proximal-end surface thereof. The distal-end section of the insertion portion 3 is inserted into the cap 5 from the opening at the proximal-end surface of the cap 5 and is fitted into the cap 5, thereby making it possible to attach the cap 5 to the insertion portion 3. The length of the cap 5 is longer than the length of the distal-end rigid section 3a, so that, in a state in which the cap 5 is attached to the distal-end section of the insertion portion 3, a distal-end section and a proximal-end section of the cap 5 respectively protrude from a distal end and a proximal end of the distal-end rigid section 3a, in the longitudinal direction.

As shown in FIG. 1B, the cap 5 has the up-down direction (first radial direction) and the left-right direction (second radial direction) that are each perpendicular to the longitudinal axis and are perpendicular to each other. As shown in FIG. 1A, the support part 9, which supports the body part 7 of the treatment tool 4 so as to be movable in the longitudinal direction, is provided at an upper side of the proximal-end section of the cap 5. The support part 9 is formed of, for example, a tube whose distal-end section is fixed to an outer circumferential surface of the proximal-end section of the cap 5 and that extends toward the opposite side from the distal end of the cap 5 along the longitudinal direction of the cap 5, and has a channel 9a that penetrates through the support part 9 in the longitudinal direction and that has an inner diameter greater than an outer diameter of the body part 7. The body part 7 is inserted through the channel 9a, is disposed along the longitudinal direction of the cap 5, and can be moved inside the channel 9a in the longitudinal direction. In this way, the support part 9 is provided on the proximal-end section of the cap 5, thereby making it possible to secure a sufficient length of a section of the body part 7 that protrudes from the support part 9 toward the distal end.

The coupling member 6 is a small-diameter member made of a material that hardly or never expands or contracts in the longitudinal direction and that has flexibility, and generates tension when a tensile force acts thereon in the longitudinal direction. For example, a thread or a metal wire is suitably used as the coupling member 6.

The coupling member 6 is inserted through a hole 4a that is provided in the treatment tool 4 and holes 5a and 5b that are provided in the cap 5, thereby coupling the cap 5 with the treatment tool 4.

Specifically, the hole 4a, which penetrates through the treatment tool 4 in a direction perpendicular to the longitudinal direction of the body part 7, is provided in the treatment tool 4 at a position between the body part 7 and the grasping part 8. The hole 4a has an inner diameter greater than an outer diameter of the coupling member 6, thus allowing the coupling member 6 to move inside the hole 4a in the longitudinal direction of the coupling member 6.

The two holes 5a and 5b, which each radially penetrate the cap 5 from an outer circumferential surface to an inner circumferential surface of the cap 5, are provided in the distal-end section of the cap 5 at two positions that are spaced in the circumferential direction and that are opposed to each other in the left-right direction. The holes 5a and 5b have inner diameters greater than the outer diameter of the coupling member 6, thus allowing the coupling member 6 to rotate, inside the holes 5a and 5b, about the center axes of the holes 5a and 5b.

The coupling member 6 has a swing section 6a that is disposed outside the distal-end section of the cap 5 and that is inserted through the hole 4a of the treatment tool 4. As shown in FIG. 1B, the swing section 6a is formed of a substantially arc-shaped section having a fixed length. Both end sections of the coupling member 6 that sandwich the swing section 6a in the longitudinal direction are inserted through the holes 5a and 5b from the outside of the cap 5 to the inside thereof and are fixed to an inner surface of the cap 5. Accordingly, the swing section 6a is supported by the cap 5 so as to be swingable about a swing axis A that passes through the two holes 5a and 5b in the left-right direction.

With the treatment tool 4 and the cap 5 being coupled via the swing section 6a, the grasping part 8 can be moved in front of the cap 5 in the up-down direction through a push-pull operation of the treatment tool 4 in the longitudinal direction.

Figure 2:
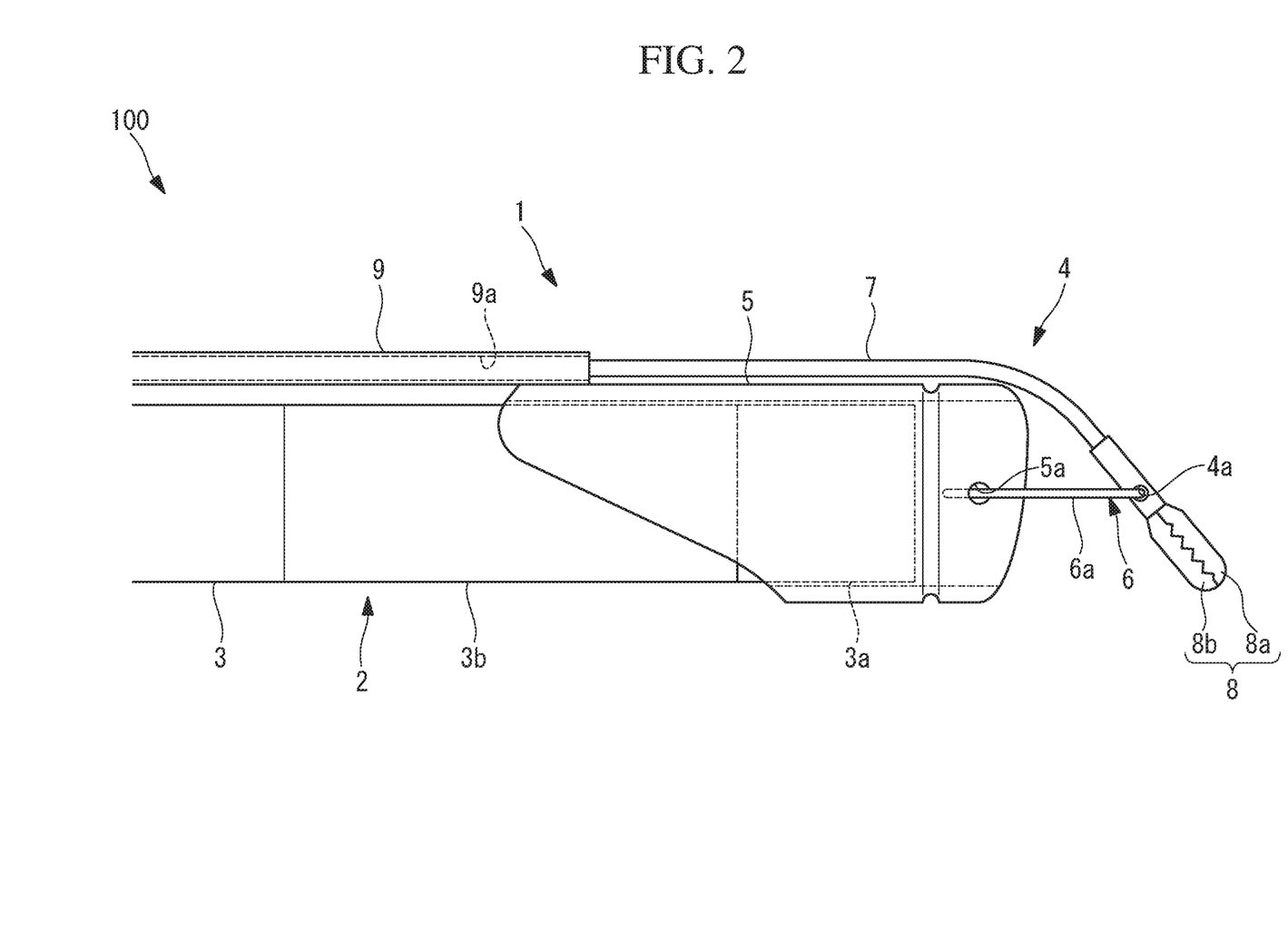
FIG. 2 is a side view of the endoscope treatment tool shown in FIG. 1A, for explaining the operation of a coupling member and a grasping part.

Specifically, as shown in FIG. 2, when the treatment tool 4 is pushed frontward in the longitudinal direction, the swing section 6a of the coupling member 6 pushed by the treatment tool 4 generates a tensile force and swings about the swing axis A from an upper side to a lower side, and the treatment tool 4, which is coupled with the swing section 6a, protrudes frontward while bending the body part 7 downward. Accordingly, the grasping part 8 moves from the upper side toward the lower side, in front of the cap 5. Furthermore, when the treatment tool 4 is pulled rearward in the longitudinal direction, the swing section 6a swings from the lower side to the upper side, and the grasping part 8 moves from the lower side to the upper side, in front of the cap 5.

Here, in a state in which a pushing force or a pulling force is not applied by the treatment tool 4, the swing section 6a is in a relaxed state, thus making it possible to easily move inside the hole 4a. Therefore, when the swing section 6a is in the relaxed state, relative movement of the treatment tool 4 and the cap 5 in the left-right direction is allowed by the flexibility of the swing section 6a and through movement of the swing section 6a inside the hole 4a. It is preferred that the hole 4a extend along the left-right direction of the cap 5, so as to allow more smooth relative movement of the treatment tool 4 and the cap 5 in the left-right direction.

Next, the operation of the thus-configured endoscope treatment tool 1 and endoscope system 100 will be described below.

In order to perform treatment on affected tissue X in the body of a patient by using the endoscope system 100 of this embodiment, as shown in FIG. 1A, the distal-end section of the insertion portion 3 is fitted into the cap 5, thereby attaching the cap 5 and the treatment tool 4 to the distal-end section of the insertion portion 3. The cap 5 and the insertion portion 3 are fixed to each other by the friction between the inner circumferential surface of the cap 5 and an outer circumferential surface of the insertion portion 3. At this time, the support part 9 and the body part 7 are disposed above the insertion portion 3, and the relative positions of the cap 5 and the insertion portion 3 about the longitudinal axis are adjusted such that the up-down direction and the left-right direction of the cap 5 are respectively aligned with the up-down direction and the left-right direction of the insertion portion 3. Furthermore, as shown in FIGS. 1A and 1B, the grasping part 8 is disposed at a position higher than the cap 5.

Next, the endoscope 2 is actuated, the assembly of the insertion portion 3 and the endoscope treatment tool 1 is inserted into the body while checking an endoscopic image in front of the distal-end surface of the insertion portion 3, and the distal end of the insertion portion 3 is disposed such that the affected tissue X is located in a lower area of the field of view of the endoscope 2. Then, the proximal-end section of the treatment tool 4, which is disposed outside the body, is pushed toward the distal end, to move the grasping part 8 frontward in the longitudinal direction, with respect to the cap 5 and the insertion portion 3.

Through the frontward movement of the grasping part 8, the coupling member 6 swings about the swing axis A, thus bending the body part 7 downward and moving the grasping part 8 from the upper side to the lower side. Therefore, in the endoscopic image, the grasping part 8 appears from the upper side and moves to the lower side toward the affected tissue X. Accordingly, merely by moving the treatment tool 4 frontward and making the grasping part 8 protrude from the distal end of the cap 5, it is possible to make the grasping part 8 reach the affected tissue X.

Figure 3:
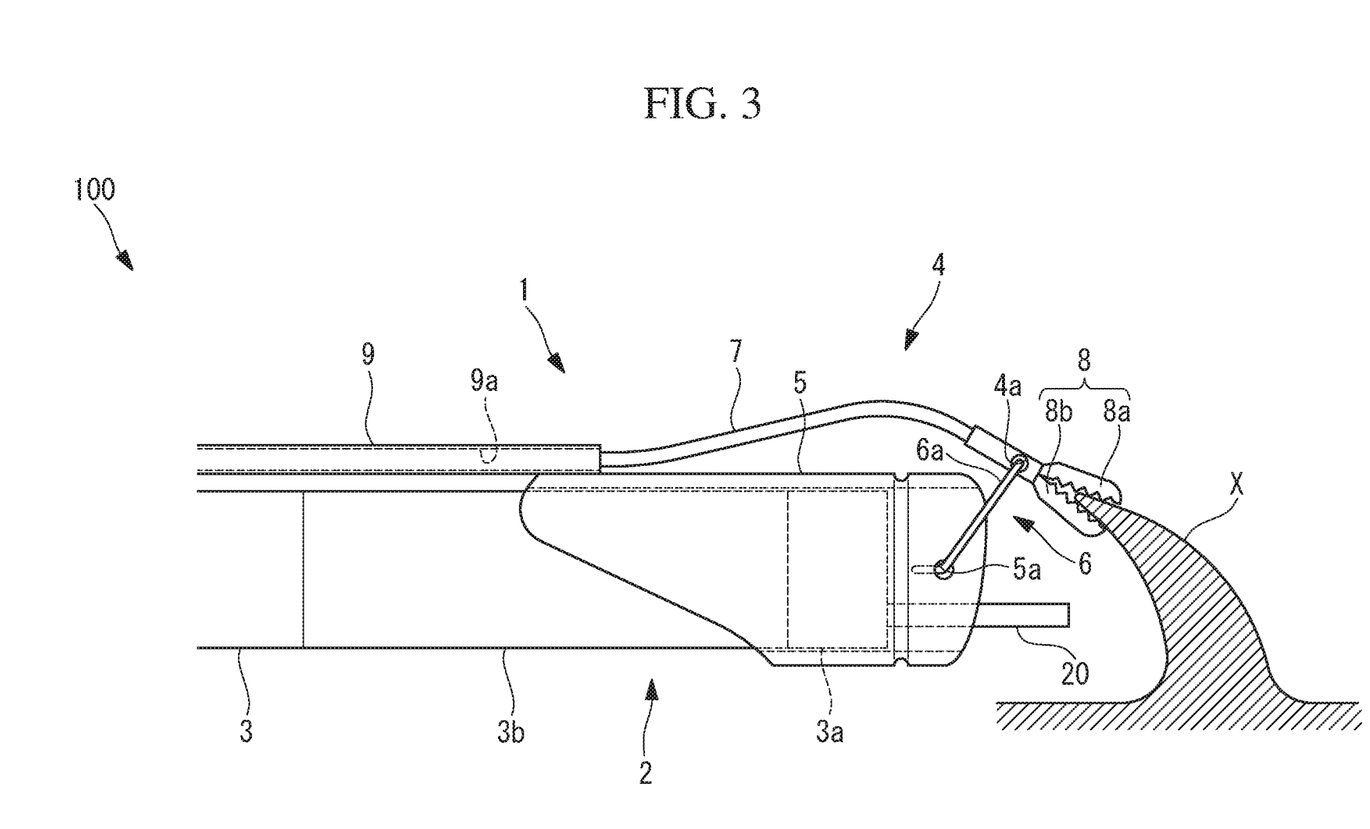
FIG. 3 is a view for explaining how to use the endoscope system shown in FIG. 1A.

Next, the grasping part 8 that has been made to reach the affected tissue X is operated, the affected tissue X is grasped by the grasping part 8, as shown in FIG. 3, and the proximal-end section of the treatment tool 4 is pulled to move the grasping part 8 toward the proximal end, thereby raising the grasped affected tissue X. In this state, the distance between the raised affected tissue X and the distal-end surface of the insertion portion 3 is secured by the distal-end section of the cap 5, which protrudes from the distal-end surface of the insertion portion 3. Next, the pulling force applied to the proximal-end section of the treatment tool 4 is released to put the swing section 6a in the relaxed state, and a treatment tool 20, such as an electric scalpel, introduced via a channel (not shown) provided in the insertion portion 3 is displaced through a bending operation of the bending section 3b in the left-right direction, thereby cutting off the raised affected tissue X by means of the treatment tool 20.

In this case, according to this embodiment, the coupling member 6, which is inserted through the hole 4a in the treatment tool 4 so as to be movable therein, couples the treatment tool 4 and the cap 5 in a manner allowing relative movement in the left-right direction. Therefore, when the bending section 3b is bent in the left-right direction, the coupling member 6 moves in the left-right direction with respect to the treatment tool 4, thereby preventing the movement of the bending section 3b in the left-right direction from being transferred to the treatment tool 4 via the coupling member 6. Accordingly, the treatment tool 4 is prevented from following the bending section 3b. Specifically, in the left-right direction, movement of the grasping part 8 and movement of the bending section 3b can be independent of each other. Accordingly, there is an advantage in that, regardless of the motion of the bending section 3b in the left-right direction when the affected tissue X is cut off, the grasping part 8 raising the affected tissue X can be kept in a stationary state, and the task of cutting off the affected tissue X can be easily performed in a state in which a tensile force is applied to the affected tissue X.

Figure 4:
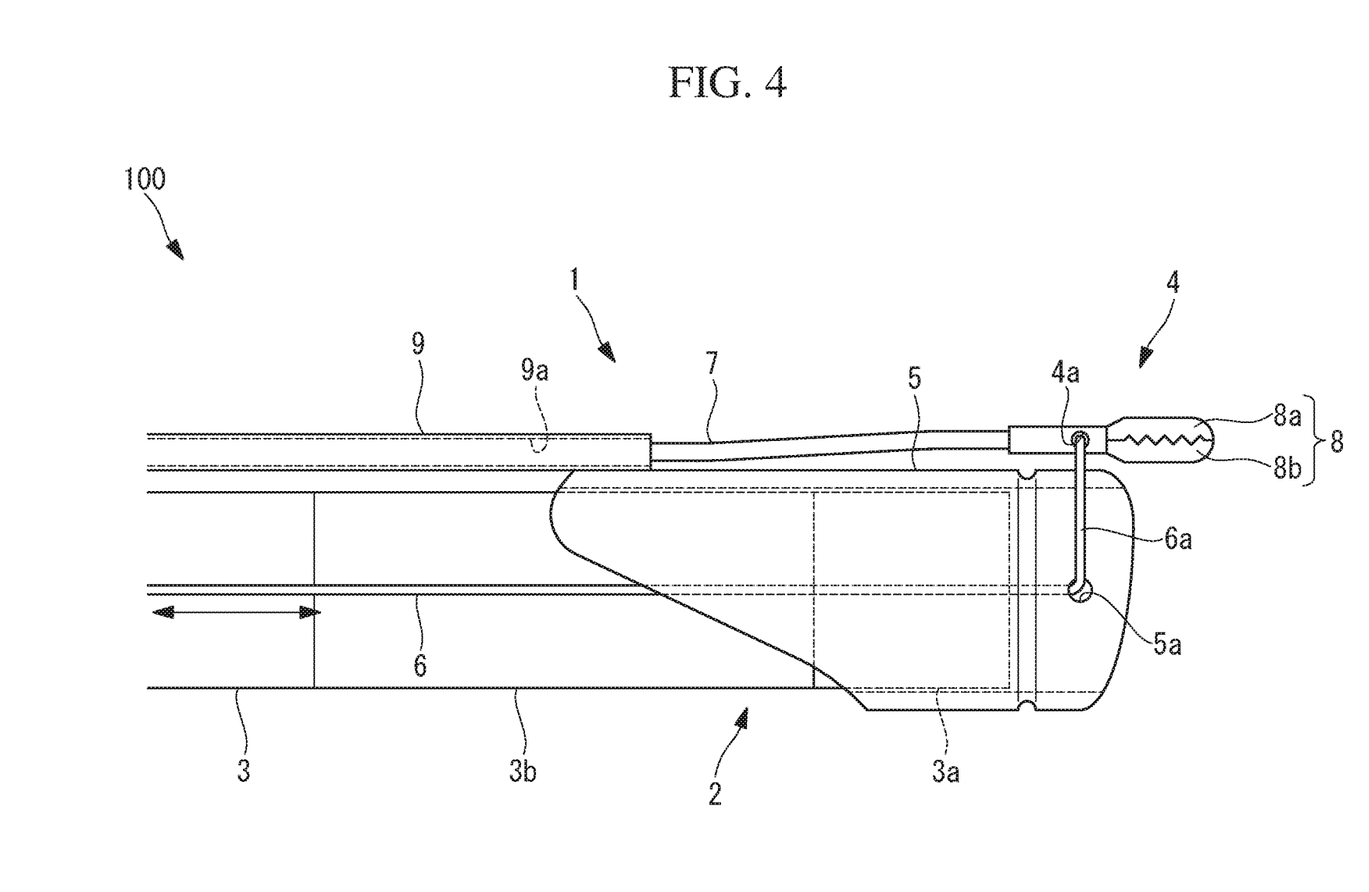
FIG. 4 is a side view of a modification of the endoscope treatment tool shown in FIG. 1A.

In this embodiment, although the coupling member 6 is inserted through the hole 4a in the treatment tool 4 so as to be movable therein, instead of this, as shown in FIG. 4, the coupling member 6 may be inserted through the holes 5a and 5b in the cap 5 so as to be movable therein in the longitudinal direction of the coupling member 6. The coupling member 6 extends from the holes 5a and 5b toward the proximal end along the longitudinal direction of the insertion portion 3, and both ends of the coupling member 6 are disposed at the proximal end of the insertion portion 3. In this case, an intermediate position of the swing section 6a in the longitudinal direction is fixed to the treatment tool 4.

By doing so, when the bending section 3b is bent in the left-right direction, both end sections of the swing section 6a move inside the holes 5a and 5b, thereby making it possible to allow relative movement of the treatment tool 4 and the cap 5 in the left-right direction.

In a modification shown in FIG. 4, the tensile force on the coupling member 6 is changed through an operation of both ends of the coupling member 6, thereby making it possible to switch the swing section 6a between a tensed state in which a tensile force is applied and a relaxed state. Specifically, when the affected tissue X is grasped by using the grasping part 8, the positions of both ends of the coupling member 6 are fixed with respect to the insertion portion 3, and a tensile force is applied to the swing section 6a of the coupling member 6 by the grasping part 8 that has been pushed forward, thereby making it possible to make the swing section 6a and the grasping part 8 swing about the swing axis A. Furthermore, after the affected tissue X is raised by the grasping part 8, both ends of the coupling member 6 are unfixed, and the length of the swing section 6a is increased a little through an operation of both ends of the coupling member 6, thus making it possible to make the swing section 6a relax. Therefore, after the affected tissue X is raised by the grasping part 8, as shown in FIG. 3, the swing section 6a is released, and the treatment tool 4 is pushed forward in the longitudinal direction, thereby making it also possible to raise the affected tissue X in a direction away from the distal end of the insertion portion 3 in the longitudinal direction.

Furthermore, in the modification shown in FIG. 4, by pushing the insertion portion 3 and the treatment tool 4 forward in the state in which the affected tissue X is raised by the grasping part 8, as shown in FIG. 3, it is possible to push the affected tissue X in a direction away from the distal end of the cap 5 by using the grasping part 8. Furthermore, in this state, the swing section 6a is relaxed through an operation of both ends of the coupling member 6, thereby making it possible to move the treatment tool 4 and the insertion portion 3 independently of each other. Therefore, while pushing the affected tissue X by using the grasping part 8, the affected tissue X can be cut off through a bending operation of the bending section 3b in the left-right direction.

Alternatively, in this embodiment, it is also possible to fix the coupling member 6 to both the treatment tool 4 and the cap 5 and to allow relative movement of the treatment tool 4 and the cap 5 in the left-right direction due to the flexibility of the swing section 6a. In this case, it is preferable that a member having high flexibility, such as a thread, be used as the coupling member 6.

Furthermore, in the modification shown in FIG. 4, at least an upper section of the cap 5 may be formed of an elastic member that can be bent radially inward.

Figure 5:
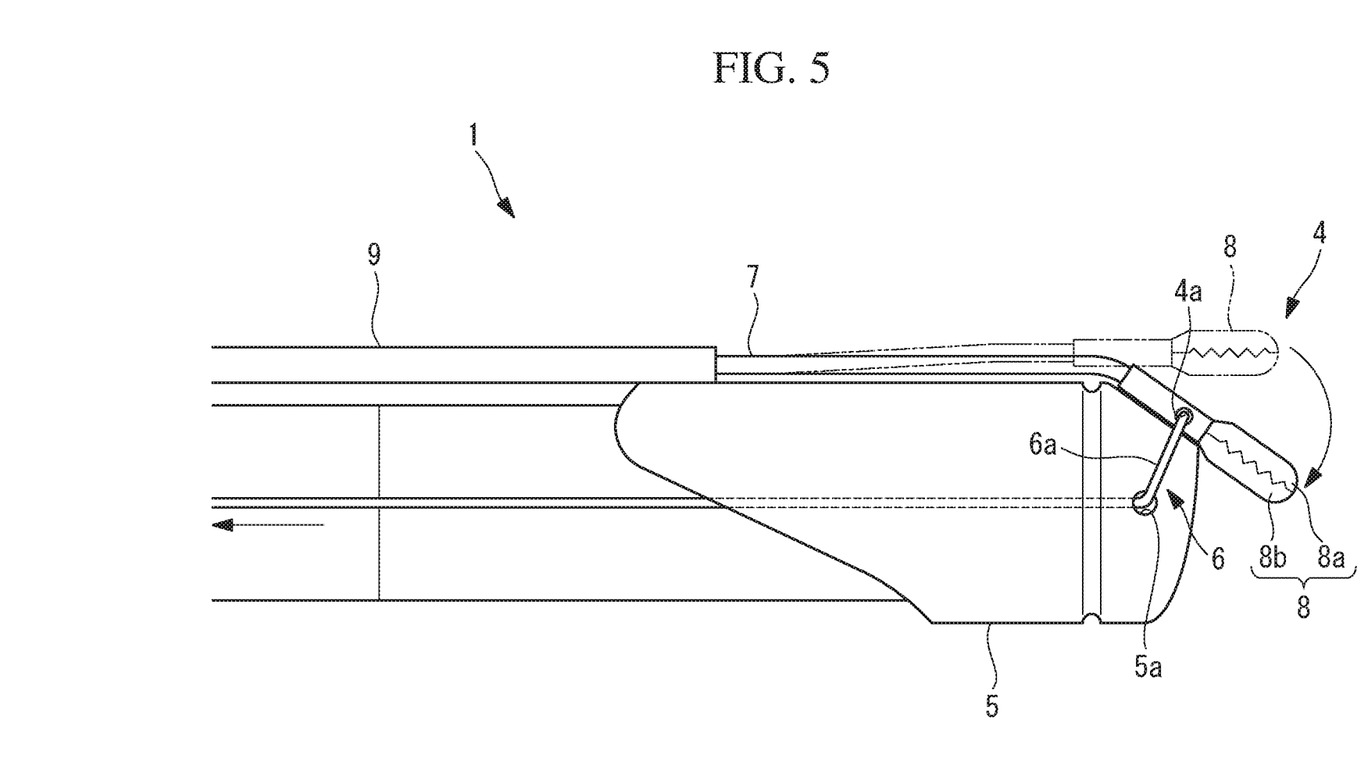
FIG. 5 is a side view of another modification of the endoscope treatment tool shown in FIG. 1A.

By doing so, as shown in FIG. 5, when both ends of the coupling member 6 are pulled, the grasping part 8 moves downward while bending the upper section of the cap 5 radially inward. Accordingly, the grasping part 8 can be disposed at a position even closer to the distal-end surface of the insertion portion 3.

Figure 6:
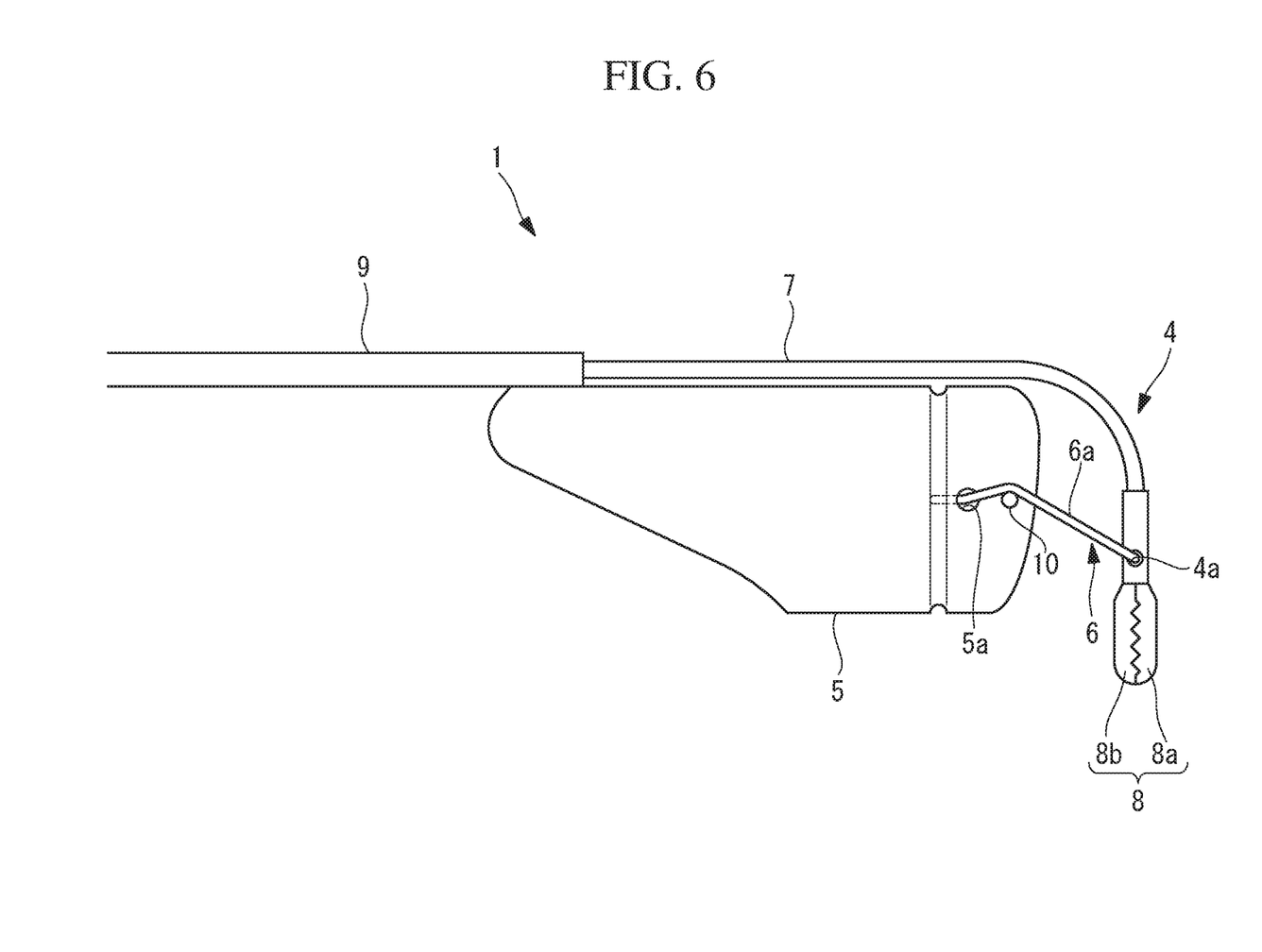
FIG. 6 is a side view of still another modification of the endoscope treatment tool shown in FIG. 1A.

In this embodiment, as shown in FIG. 6, a protrusion 10 that radially protrudes from the outer circumferential surface of the cap 5 may be provided thereon. The protrusion 10 is provided so as to be closer to the distal end than the swing axis A (i.e., the holes 5a and 5b) is, and is preferably provided at a position aligned with or higher than the swing axis A in the up-down direction.

By doing so, when the swing section 6a swings downward, an intermediate position of the swing section 6a is caught by the protrusion 10 and is bent, thereby making it possible to dispose the grasping part 8 at a position even closer to the distal-end surface of the insertion portion 3.

As a result, the above-described embodiment leads to the following aspects.

A first aspect of the present invention provides an endoscope treatment tool including: a cylindrical cap that is attached to an outer side of a distal-end section of an endoscope, the cylindrical cap having a first radial direction and a second radial direction intersecting each other; a treatment tool that has, at a distal end, a grasping part for grasping living tissue, the treatment tool being disposed, at an outer side of the cap in the first radial direction, along a longitudinal direction of the cap, the treatment tool being supported by the cap, at a position closer to a proximal end than the grasping part is, so as to be movable in the longitudinal direction; and a coupling member that couples the treatment tool with the cap, the coupling member having a linear shape, wherein the coupling member has a swing section that is disposed outside the cap and that is supported by the cap so as to be swingable about a swing axis extending in the second radial direction; and the swing section couples the cap with the treatment tool so as to allow relative movement in the second radial direction, and, in response to pressed forward in the longitudinal direction by the treatment tool moved forward in the longitudinal direction, swings about the swing axis while generating a tensile force and bending the treatment tool inward in the first radial direction.

According to this aspect, when the cap is attached to the distal-end section of the endoscope such that the first radial direction of the cap and the up-down direction of the endoscope become substantially parallel to each other and such that the treatment tool is disposed at an upper side of the endoscope, the treatment tool is disposed outside the endoscope along the longitudinal direction of the endoscope. Then, when the treatment tool is moved forward in the longitudinal direction with respect to the cap and the endoscope, the swing section of the coupling member, which couples the treatment tool with the cap, swings about the swing axis, which intersects the up-down direction of the endoscope, toward the lower side of the endoscope, while bending the treatment tool downward. Accordingly, the grasping part moves from the upper side of the endoscope toward the lower side thereof. Therefore, merely by pushing the treatment tool forward with respect to the cap and the endoscope, it is possible to bring the grasping part close to a target section of the living tissue located in a lower area in the field of view of the endoscope and to grasp the target section. Furthermore, merely by pulling the treatment tool rearward with respect to the cap and the endoscope, the target section grasped by the grasping part can be raised.

In this case, because the treatment tool and the cap are coupled via the coupling member in a manner allowing relative movement in the second radial direction, which intersects the up-down direction of the endoscope, i.e., in the left-right direction of the endoscope, the treatment tool and the endoscope can be moved independently of each other. Specifically, when the distal end of the endoscope is moved in the left-right direction through an operation of the bending section, the grasping part grasping the target section stays stationary without following the movement of the endoscope. Accordingly, while the target section, which is raised by the grasping part, is made to stay stationary, treatment, such as cutting, can be easily performed on the target section by operating the endoscope.

In the above-described first aspect, the treatment tool may have a hole that is provided at a position closer to the proximal end than the grasping part is and that penetrates in a direction intersecting a longitudinal direction of the treatment tool; the swing section may be inserted through the hole so as to be movable in a longitudinal direction of the swing section; and both end sections of the coupling member that sandwich the swing section in a longitudinal direction thereof may be supported by the cap at two places opposed to each other in the second radial direction, so as to be swingable about the swing axis.

By doing so, relative movement of the treatment tool and the cap in the second radial direction can be realized through movement of the swing section inside the hole in the treatment tool. Furthermore, the swing section can swing about the swing axis passing through the two places on the cap, at which both end sections of the swing section are supported.

In the above-described first aspect, the cap may have two holes that penetrate in a radial direction of the cap, at two places opposed to each other in the second radial direction; an intermediate position of the swing section in a longitudinal direction thereof may be fixed to the treatment tool; and both end sections of the coupling member that sandwich the swing section in a longitudinal direction thereof may be inserted through the two holes so as to be movable in a longitudinal direction of the coupling member.

By doing so, relative movement of the treatment tool and the cap in the second radial direction can be realized through movement of the coupling member inside the holes in the cap. Furthermore, the swing section can swing about the swing axis passing through the two holes in the cap, into which both end sections of the swing section are inserted.

In the above-described first aspect, the swing section of the coupling member may have a fixed length.

By doing so, the movement track of the grasping part through swing of the swing section can be fixed.

In the above-described first aspect, the swing section of the coupling member may be switched from a tensed state in which the tensile force is generated to a relaxed state.

By doing so, after the target section is grasped by the grasping part, the swing section is switched from the tensed state to the relaxed state, and the treatment tool is pushed forward in the longitudinal direction while the target section is grasped by the grasping part, thereby making it possible to raise the target section also in a direction away from the distal end of the endoscope in the longitudinal direction.

In the above-described first aspect, the cap may support the treatment tool at a proximal-end section of the cap.

By doing so, it is possible to secure a long length of a section that is bent when the treatment tool is pushed forward in the longitudinal direction.

A second aspect of the present invention provides an endoscope system including: an endoscope; and one of the above-described endoscope treatment tools.

According to the present invention, an advantageous effect is afforded in that a treatment tool guided into the field of view of an endoscope via the outside of the endoscope is operated independently of the movement of the endoscope, thereby making it possible to easily perform treatment.

REFERENCE SIGNS LIST 1 endoscope treatment tool
2 endoscope
3 insertion portion
3a distal-end rigid section
3b bending section
4 treatment tool
4a hole
5 cap
5a, 5b hole
6 coupling member
6a swing section
7 body part
8 grasping part (grasper)

8a, 8b grasping piece (grasper)
9 support part
9a channel
10 protrusion
20 treatment tool
A swing axis
X affected tissue (living tissue)

The invention claimed is:

1. An endoscope treatment tool comprising:
a cylindrical cap configured to be attached to an outer side of a distal-end section of an endoscope;
a treatment tool having a grasper for grasping tissue at a distal end thereof, the treatment tool being disposed at an outer side of the cap in a first radial direction of the cap and along a longitudinal direction of the cap, the treatment tool being supported by the cap so as to be movable in the longitudinal direction; and
an elongated coupling member configured to couple the treatment tool with the cap such that the grasper moves between a first position at the outer side of the cap and a second position at which the grasper is moved distally of the cap,
wherein a portion of the coupling member comprises a swing portion disposed outside the cap, and the swing portion is configured to be supported by the cap so as to be swingable about a swing axis extending in a second radial direction intersecting with the first radial direction,
wherein the swing portion is configured to:
couple the cap with the treatment tool so as to allow movement of the swing portion relative to the cap in the second radial direction; and
swing about the swing axis while generating a tensile force and bending the treatment tool inward in the first radial direction when the swing portion is pressed forward in the longitudinal direction by the treatment tool being moved forward in the longitudinal direction, and
wherein the cap comprises, on an outer circumferential surface of the cap, a protrusion that rotatably supports the swing portion so as to allow the swing portion to be bent by bringing the swing portion into contact with the protrusion.

2. The endoscope treatment tool according to claim 1, wherein the treatment tool has a hole provided proximally relative to the grasper and the hole penetrates in a direction intersecting a longitudinal direction of the treatment tool.

3. The endoscope treatment tool according to claim 1, wherein the cap has two holes that penetrate in a radial direction of the cap, at two places opposed to each other in the second radial direction.

4. The endoscope treatment tool according to claim 3, wherein the swing portion of the coupling member can be switched from a tensed state in which the tensile force is generated to a relaxed state.

5. The endoscope treatment tool according to claim 1, wherein the swing portion has a fixed length.

6. The endoscope treatment tool according to claim 1, wherein the cap supports the treatment tool at a proximal-end section of the cap.

7. The endoscope treatment tool according to claim 1, wherein the grasper is configured to be movable relative to the cap where the swing portion of the coupling member comes into contact with the protrusion.

8. The endoscope treatment tool according to claim 1, wherein the protrusion extends radially outward on the outer circumferential surface of the cap.

9. The endoscope treatment tool according to claim 1, wherein the coupling member comprises a thread.

10. An endoscope treatment tool comprising:
a cylindrical cap configured to be attached to an outer side of a distal-end section of an endoscope;
a treatment tool having a grasper for grasping tissue at a distal end thereof, the treatment tool being disposed at an outer side of the cap in a first radial direction of the cap and along a longitudinal direction of the cap, the treatment tool being supported by the cap so as to be movable in the longitudinal direction of the cap; and
a coupling member configured to couple the treatment tool with the cap such that the grasper moves between a first position at which the grasper is disposed distally of the cap and a second position at the outer side of the cap, the coupling member being formed by an elongated member,
wherein a portion of the coupling member comprises a swing portion disposed outside the cap, and the swing portion is configured to be supported by the cap so as to be swingable about a swing axis extending in a second radial direction intersecting with the first radial direction,
wherein the swing section portion is configured to:
have a relaxed state and a tensed state;
couple the cap with the treatment tool so as to allow relative movement of the swing portion relative to the cap in the second radial direction in the relaxed state without being pressed and without being pulled by the treatment tool; and
swing about the swing axis by bending the treatment tool inward in the first radial direction in the tensed state while being pressed forward in the longitudinal direction by the treatment tool, and
wherein the cap comprises, on an outer circumferential surface of the cap, a protrusion that rotatably supports the swing portion so as to allow the swing portion to be bent by bringing the swing portion into contact with the protrusion.

11. The endoscope treatment tool according to claim 10, wherein the treatment tool has a hole that is provided proximally relative to the grasper and the hole penetrates in a direction intersecting a longitudinal direction of the treatment tool.

12. The endoscope treatment tool according to claim 10, wherein the cap has two holes that penetrate in a radial direction of the cap, at two places opposed to each other in the second radial direction.

13. The endoscope treatment tool according to claim 12, wherein the swing portion is configured to be switched between the relaxed state and the tensed state by switching between a state in which the ends of the coupling member are unfixed and a state in which the ends of the coupling member are fixed.

14. The endoscope treatment tool according to claim 12, wherein the swing portion is configured to be switched from the tensed state to the relaxed state by unfixing the ends of the coupling member and moving the coupling member in the longitudinal direction of the endoscope to lengthen the swing portion.

15. The endoscope treatment tool according to claim 10, wherein the swing portion of the coupling member can be switched from the tensed state in which the tensile force is generated to the relaxed state.

16. The endoscope treatment tool according to claim 10, wherein the swing portion has a fixed length.

17. The endoscope treatment tool according to claim 10, wherein the cap supports the treatment tool at a proximal-end section of the cap.

18. The endoscope treatment tool according to claim 10, wherein the grasper is configured to be movable relative to the cap where the swing portion of the coupling member comes into contact with the protrusion.

19. The endoscope treatment tool according to claim 10, wherein the protrusion extends radially outward on the outer circumferential surface of the cap.

20. The endoscope treatment tool according to claim 10, wherein the coupling member comprises a thread.

* * * * *